United States Patent
Remde

(10) Patent No.: US 8,118,782 B2
(45) Date of Patent: Feb. 21, 2012

(54) INSULIN PUMP WITH REPLACEMENT CAPABILITIES

(75) Inventor: Axel Remde, Luetzelfueh (CH)

(73) Assignee: Roche Diagnostics International AG, Steinhausen (CH)

( * ) Notice: Subject to any disclaimer, the term of this patent is extended or adjusted under 35 U.S.C. 154(b) by 63 days.

(21) Appl. No.: 12/875,713

(22) Filed: Sep. 3, 2010

(65) Prior Publication Data

US 2011/0218495 A1   Sep. 8, 2011

Related U.S. Application Data

(63) Continuation of application No. PCT/EP2009/001458, filed on Mar. 2, 2009.

(30) Foreign Application Priority Data

Mar. 3, 2008 (EP) ................................. 08405064

(51) Int. Cl.
*A61M 5/142* (2006.01)

(52) U.S. Cl. .......... 604/151; 607/60; 709/232; 709/237; 705/2

(58) Field of Classification Search ................ 604/151; 607/2, 60; 709/232, 237, 248; 705/2
See application file for complete search history.

(56) References Cited

U.S. PATENT DOCUMENTS

| | | | |
|---|---|---|---|
| 2007/0032891 A1* | 2/2007 | Choi | 700/65 |
| 2007/0124002 A1 | 5/2007 | Estes et al. | |
| 2007/0233206 A1* | 10/2007 | Frikart et al. | 607/60 |
| 2008/0014947 A1* | 1/2008 | Carnall | 455/437 |
| 2008/0051738 A1 | 2/2008 | Griffin | |
| 2009/0164667 A1* | 6/2009 | Zhang et al. | 709/248 |

FOREIGN PATENT DOCUMENTS

| | | |
|---|---|---|
| WO | 0010628 A2 | 3/2000 |
| WO | 2006097453 A1 | 9/2006 |
| WO | 2007056592 A2 | 5/2007 |

OTHER PUBLICATIONS

International Search Report, completion date of Aug. 5, 2009 for International Application No. EP 09001458, pp. 1-8.
Written Opinion, mailing date of Nov. 8, 2009 for International Application No. EP 09001458, pp. 1-8.

* cited by examiner

*Primary Examiner* — Quynh-Nhu H Vu
(74) *Attorney, Agent, or Firm* — Dinsmore & Shohl LLP

(57) ABSTRACT

Insulin delivery systems include a first insulin pump and a second insulin pump, wherein each pump includes a memory configured to store an infusion program, a control unit configured to control operation of the pump, and a communication interface for data exchange with the other pump, wherein the control unit of the first insulin pump is configured monitor, a status of the first insulin pump, activate a search for the presence of the second insulin pump when a predetermined status is assumed, and, upon detection of the presence of the second insulin pump, transmit, via the communication interface of the first insulin pump, the infusion program stored, and the control unit of the second insulin pump is configured to search for the presence of the first insulin pump, and, upon detection of the presence of the first insulin pump, receive and store, the infusion program.

18 Claims, 4 Drawing Sheets

INSULIN PUMP WITH REPLACEMENT CAPABILITIES

CROSS REFERENCE TO RELATED APPLICATIONS

This application is a continuation of International Application No. PCT/EP2009/001458 filed Mar. 2, 2009 which claims priority to European Patent Application No. EP 08 405 064.0 filed on Mar. 3, 2008, both of which are incorporated by reference herein.

TECHNICAL FIELD

The invention relates to insulin delivery systems and, more specifically, insulin delivery systems including a first insulin pump and a second insulin pump allowing for the replacement of the first insulin pump by the second insulin pump via autonomous program transfer.

BACKGROUND

Remotely controlled insulin pumps may be used for the continuous subcutaneous infusion of insulin to patients with diabetes. The insulin, which may be present in a reservoir of the insulin pump, can be conveyed into the patient's body according to a patient and time-of-day dependent basal delivery schedule via a subcutaneous cannula. In addition to this basal delivery, bolus insulin delivery may be performed out of the same reservoir on demand such as, for example, for compensating carbohydrate intake and for correcting undesirably raised blood glucose values. Some modern insulin pumps have programmable remote controllers that can comprise a design similar to a cell phone or a PDA. Alternatively, a standard device such as a cell phone or a PDA may be used as the remote controller itself. For those insulin pumps, the user interface of the insulin pump itself may be limited or missing.

Insulin pumps which are designed to be fully remote controlled may be disposable pumps which are designed to be used for a number of days and to be disposed afterwards. When such a pump is replaced, an infusion program including all required control data, such as the basal delivery schedule, the date and the time of day may be transferred onto the new pump from the remote controller. Prior to this transfer, the memory of the insulin pump comprises the control firmware but no patient-specific infusion program.

Some insulin pumps can be designed as patch pumps which are carried by the patient directly at the infusion site and can be fixed to the skin by an adhesive layer. Those pumps can comprise a cannula and an automatic inserter which automatically inserts the cannula into to patient's subcutaneous tissue from an initially retracted position inside the housing. Those pumps may also be provided with a readily built-in reservoir which is filled by the patient prior to use and readily built-in battery. After a using time of some days, the pump can be disposed as a whole.

For fully remote controlled insulin pumps, the remote controller may be required for all user operations such as programming the delivery of an insulin bolus or replacing the pump by a new one. However, in some situations a remote controller may not be available. This may be the case, for example, when the remote controller is defective, lost or forgotten, e.g., when traveling. Accordingly, a need exists for alternative insulin delivery systems such as those including a first insulin pump and a second insulin pump for continuous therapy.

SUMMARY

In one embodiment, an insulin delivery system includes a first insulin pump and a second insulin pump. Each of the first insulin pump and the second insulin pump includes a memory configured to store an infusion program, a control unit configured to control operation of the insulin pump, and a communication interface for data exchange with the other of the first insulin pump and the second insulin pump. The control unit of the first insulin pump is configured to autonomously perform the steps of monitoring, during operation of the first insulin pump according to the infusion program, a status of the first insulin pump, activating a search for the presence of the second insulin pump when a predetermined status is assumed by the first insulin pump, and, upon detection of the presence of the second insulin pump, transmitting, via the communication interface of the first insulin pump, the infusion program stored in the memory of the first insulin pump to the second insulin pump. The control unit of the second insulin pump is configured to perform the steps of searching for the presence of the first insulin pump, and, upon detection of the presence of the first insulin pump, performing the steps of receiving, via the communication interface of the second insulin pump, an infusion program from the first insulin pump and storing the infusion program in the memory of the second insulin pump.

In another embodiment, a method for replacing a first insulin pump by a second insulin pump, includes operating the first insulin pump according to an infusion program stored in a memory of the first insulin pump, and controlling the first insulin pump to autonomously perform the steps of activating a search for the presence of the second insulin pump, and, upon detection of the presence of the second insulin pump, and transmitting, via communication interfaces of the first insulin pump and the second insulin pump, the infusion program from the first insulin pump to the second insulin pump.

In yet another embodiment An insulin pump includes a communication interface for data exchange with a replacement pump, a memory which can be configured to store an infusion program, and a control unit which is configured to control operation of the insulin pump. The control unit can be configured to autonomously perform the steps of monitoring, during operation of the infusion pump according to the infusion program, a status of the insulin pump, activating a search for the presence of the replacement pump when a predetermined status is assumed by the insulin pump, and transmitting, upon detecting the presence of the replacement pump, via the communication interface, the infusion program stored in the memory to the replacement pump.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings where like structure is indicated with like reference numerals and in which:

DETAILED DESCRIPTION

Insulin pumps and insulin delivery systems as disclosed herein may allow a diabetic patient to continue their insulin pump therapy if a first insulin pump has to be replaced. The insulin pumps may be of any general type of insulin pump. For example, in one embodiment, disposable patch pumps may be used. However, various other insulin pumps may additionally or alternatively be implemented as will become appreciated herein.

Figure 1A:
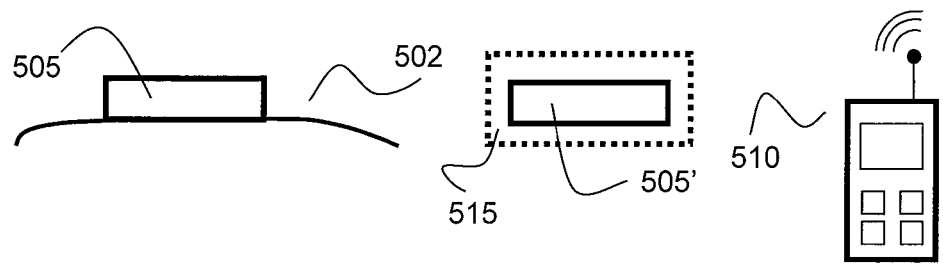
FIG. 1 schematically depicts a replacement procedure of a first insulin pump by a second insulin pump according to one or more embodiments shown and described herein.
Figure 1B:
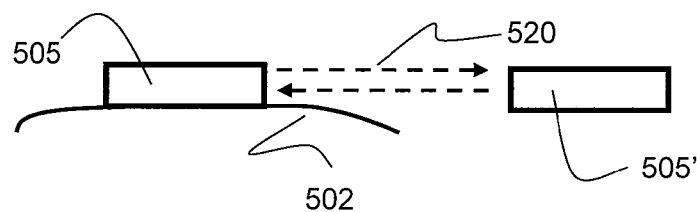
Figure 1C:
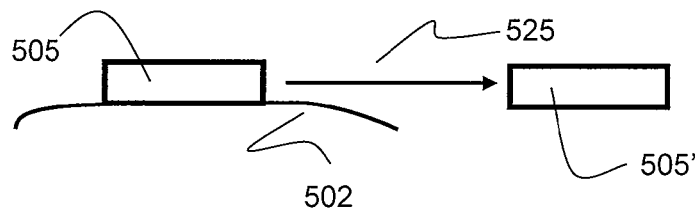
Figure 1D:
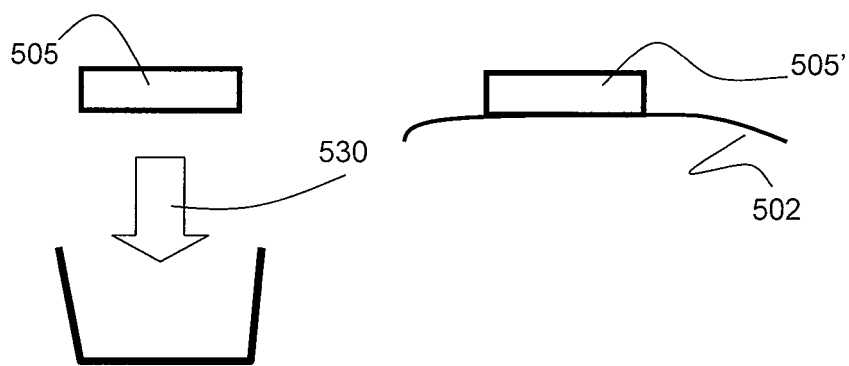
Figure 2:
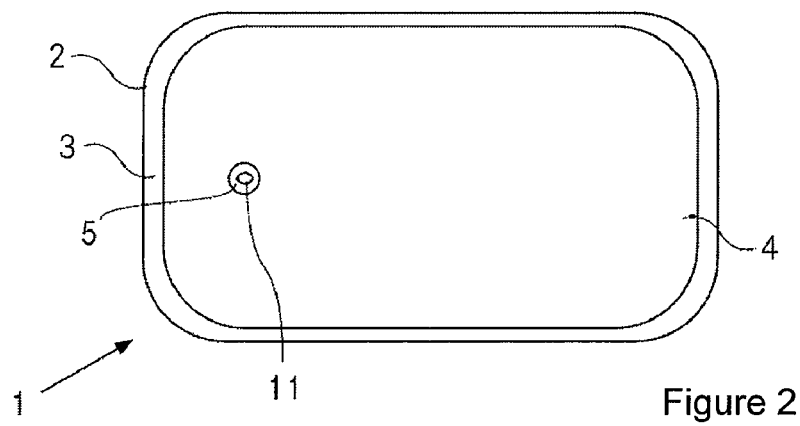
FIG. 2 depicts a plan view of the rear face of an insulin pump according to one or more embodiments shown and described herein.
Figure 3:
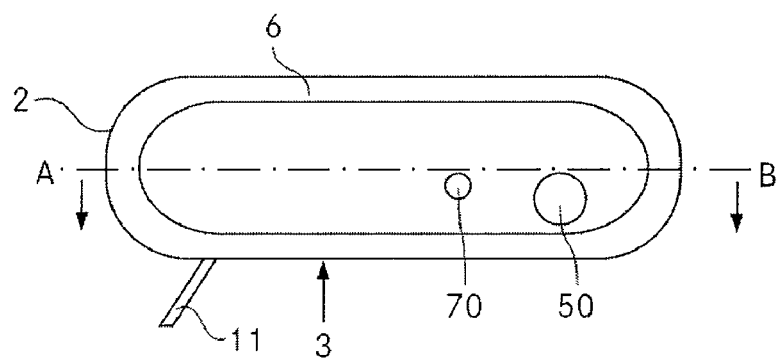
FIG. 3 depicts a side view of the insulin pump from FIG. 2 according to one or more embodiments shown and described herein.
Figure 4:
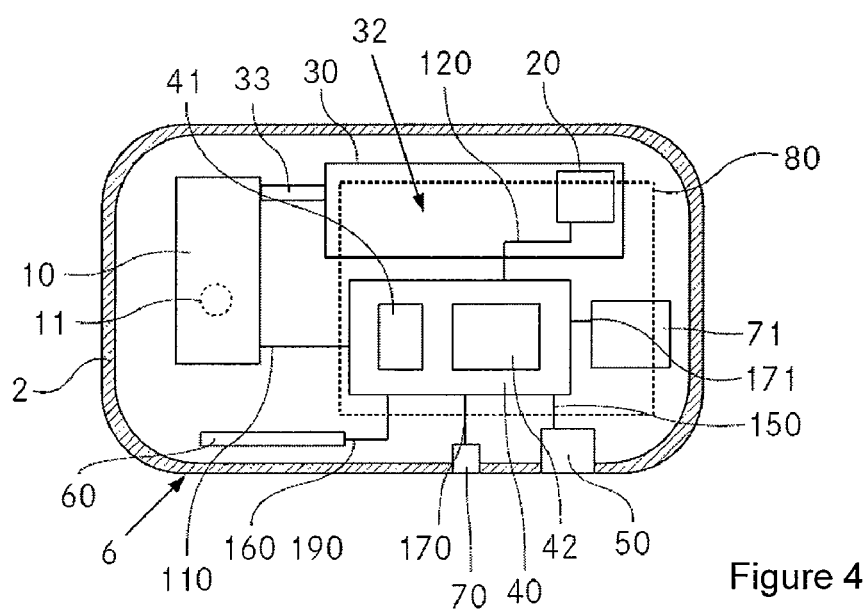
FIG. 4 depicts a schematic view of the inner area and the functional elements of the insulin pump in a cross section along the line A-B in FIG. 2 according to one or more embodiments shown and described herein.

Referring now to FIGS. 1-6, in one embodiment, an insulin delivery system may generally comprise a first insulin pump 1, 505 (also referred to as a source pump) and a second insulin pump 1, 505' (also referred to as a replacement pump). Referring specifically to FIGS. 2-4, the first insulin pump 1 and the second insulin pump 1 may generally comprise a housing 2 in the form of a hollow parallelepipedal body with rounded corners and edges or any other form operable to house the necessary components as should become appreciated herein. In other embodiments, the shape of the housing 2 may comprise a more ergonomic form, such that the insulin pump 1 is easier to handle and protrudes as little as possible on the patient's body. In one embodiment, such as that illustrated in FIG. 2, the underside 3 of the housing 2 may be substantially rectangular and have rounded corners; however any other operable configuration may alternatively or additionally be utilized. In one particular embodiment, except for a narrow edge area, the underside 3 may also be covered with an adhesive coating 4, which may be provided for securing the insulin pump 1 to the body of a patient, e.g. in the abdominal area. As also illustrated in FIG. 2, a circular opening 5 may be formed in the underside 3 of the housing 2, such as centrally on the left-hand side of the housing 2, or anywhere else about the housing 2. This opening 5 may serve as a passage for the cannula 11 arranged in the automatic inserter 10 in the interior of the housing 2. The automatic inserter 10 may be designed such that it can deploy the cannula 11 from a completely retracted position in the interior of the housing 2 and through the opening 5, in an oblique direction with respect to the underside 3, several millimeters from the opening 5.

Referring now to FIG. 3, a side view of a first lengthwise side 6 of the insulin pump 1 depicts the cannula 11 in the fully deployed position. The cannula 11 may be made from any soft and biocompatible material, such as Teflon or the like, and protrude down to the left in an oblique direction with respect to the underside 3 of the insulin pump 1. Moreover, in one exemplary embodiment, in a lower area at the right of the lengthwise side 6 of the housing 2, an infrared interface 50 may be arranged in a recess of the housing 2 and be used to detect another insulin pump. To the left alongside it, an optional light-emitting diode 70 may be located as a status indicator in another recess of the housing 2.

Referring now to FIG. 4, the inner structure of the insulin pump 1 is schematically depicted in a cross section through the housing 2 of the insulin pump 1 along the line A-B from FIG. 3. In one embodiment, the automatic inserter 10 may be arranged on the left-hand side, and the inserter 10 communicates with an insulin reservoir 30 via a tube 33. The insulin reservoir 30 itself may be arranged in an upper edge area along the upper and second lengthwise side of the housing 2. Inside the automatic inserter 10, a tubing system (not shown) may connect the cannula 11 to the tube 33. The insulin 32 present in the insulin reservoir 30 may thereby be conveyed to the cannula 11 through the tube 33 and the automatic inserter 10 by means of a delivery device 20 coupled to the insulin reservoir. In one embodiment, the delivery device 20 may comprise, for example, a plug (not shown in FIG. 4) which may be moved or forced into the insulin reservoir 30 by a spindle mechanism, thus displacing a plug of the insulin reservoir. The insulin 32 located in the insulin reservoir 30 may thus be displaced by the plug and, as has been described above, conveyed through the tube 33 into the cannula 11. In one embodiment, in order to determine the filling state of the insulin reservoir 30, it may be possible to count the control impulses sent to a stepping motor of the spindle drive and/or to provide a motor with an encoder. In another embodiment, the filling state of the insulin reservoir 30 may be determined by using a filling state sensor arranged on the insulin reservoir 30. By way of a control line connecting the filling state sensor to the control unit 40, the filling state determined in the insulin reservoir 30 by the filling state sensor can be transmitted to the control unit 40.

Moreover, in one exemplary embodiment, a sound generator 71, such as a loudspeaker or buzzer, may be integrated in the area before the right-hand narrow side of the housing 2 as an additional status indicator and for alarming purposes. The infrared interface 50, already described with respect to FIG. 3, may be arranged on the lower and first lengthwise side 6, in a suitable recess in the housing 2 to the right of the centre. To its left, the light-emitting diode 70, arranged on the lower lengthwise side, may also be arranged in a corresponding further recess in the housing 2. To the left of the centre of the lower and first lengthwise side 6, a radiofrequency interface 60 may also arranged in the interior of the housing 2. In one embodiment, another communication interface can be provided instead of the radiofrequency interface 60. For example, an infrared interface can also be used for transfer of the program as will become appreciated herein.

Referring still to FIGS. 2-4, the first insulin pump 1 and the second insulin pump 1 may each further comprise a memory 42, a control unit 40 and a communication interface 60. In one exemplary embodiment, the control unit 40 with a microprocessor or microcontroller 41 and the memory unit 42 may be arranged in the central area in the interior of the insulin pump 1. For example, the control unit 40 may be connected to the inserter via a first control line 110, such that the insertion and optionally also the retraction of the cannula 11 can be controlled by the control unit 40. A second control line 120 between the control unit 40 and the delivery device 20 may permit the transfer of control impulses from the control unit 40 to the delivery device 20. In such an embodiment, the sound generator 71 discussed above may be connected by a third control line 171 to the control unit 40 and can thus be activated by the latter. Furthermore, the light-emitting diode 70 may likewise be connected by a fourth control line 170 to the control unit 40 and can be switched on or off by the latter. The fifth control line 150 between the infrared interface 50 and the control unit 40 may permit the activation and deactivation of the infrared interface 50 and also the data transfer between infrared interface 50 and control unit 40. Finally, the radiofrequency interface 60 may be connected to the control unit 40 by the sixth control line 160. Between control unit 40 and radiofrequency interface 60, data may be transferred and the radiofrequency interface 60 can be activated or deactivated. In one embodiment, above the sectional plane illustrated in FIG. 4, a battery 80 may be present for the insulin pump 1 (indicated by the broken line). The cabling of the battery 80 may be configured in a manner known.

The memory unit 42 may be provided both for storage of a infusion program and also for holding a protocol file (such as selected operating parameters of the insulin pump) or log file of the insulin pump. As used herein, the term 'infusion program' is used in the sense of data and parameters necessary for the insulin pump to operate as intended. The infusion program may comprise a patient-specific basal delivery schedule as well as the current time of day and/or the current date. For example, an operation mode in which the first insulin pump 1 or the second insulin pump 1 performs delivery according the infusion program may be referred to as the 'delivery mode'.

In one particular embodiment, the memory 42 may specifically be configured to store the infusion program, the control unit 40 may be configured to control the operation of either the first insulin pump 1 or the second insulin pump 1. The communication interface 60 may be configured for data exchange with the other of the first insulin pump 1 and the second insulin pump 1. In one embodiment, the control unit 40 of the first insulin pump 1 may be configured to autonomously perform the steps of activating a search for the presence of the second insulin pump 1, and, upon detection of the presence of the second insulin pump 1 transmitting, via the communication interface 60 of the first insulin pump 1, the infusion program stored in the memory 42 of the first insulin pump 1 to the second insulin pump 1.

Furthermore, the control unit 40 of the second insulin pump 1 may be configured to perform the steps of searching for the presence of the first insulin pump 1, and, upon detection of the presence of the first insulin pump 1 performing the steps of receiving, via the communication interface 60 of the second insulin pump 1, an infusion program from the first insulin pump 1, and storing the infusion program in the memory 42 of the second insulin pump 1.

In one embodiment of continuing therapy via a second insulin pump 1, the infusion program may be the basis for an appropriate insulin infusion according to the patient's individual need. Thus, in contrast to the basal administration, the additional insulin boli may also be administered whenever required by alternative means, such as an insulin pen or a syringe. Therefore, an insulin infusion system according to one embodiment may allow the patient to continue his or her therapy even if no remote controller is present and/or if the insulin pumps have no user interface for initiating or modifying the drug administration. In one embodiment of the insulin infusion system, the pump replacement may allow for a simple use thereof via the detection of the presence of the second insulin pump and the subsequent transfer of the infusion program being carried out autonomously without the need for user interactions.

In one exemplary embodiment, the first insulin pump 1 and the second insulin pump 1 of the system may be designed or configured such that the first insulin pump 1 only has the capability of transmitting the infusion program to the second insulin pump 1 and the second insulin pump 1 only has the capability of receiving an infusion program from the first insulin pump 1. Alternatively, either of the two insulin pumps 1 may both transmit and receive an infusion program. In particular embodiments, however, the first insulin pump 1 and the second insulin pump 1 may comprise identical insulin pumps, each being generally capable of acting as the first insulin pump 1 or as the second insulin pump 1. As discussed above, both insulin pumps 1 may comprise disposable insulin pumps which may be provided in a kit of, for example, ten individual pumps. Alternatively, the first insulin pump 1 may, for example, be the generally used insulin pump while the second insulin pump 1 may be an additional backup pump.

In yet another embodiment, the insulin pump 1 may generally comprise a communication interface for data exchange with a replacement pump, a memory which is configured to store an infusion program, and a control unit which is configured to control operation of the insulin pump 1. The control unit of the insulin pump 1 may be configured to autonomously perform the steps of activating a search for the presence of the replacement pump, and transmitting, upon detecting the presence of the replacement pump, via the communication interface the infusion program stored in the memory to the replacement pump.

In one embodiment, the insulin pump 1 may comprise an insulin pump 1 of an insulin infusion system and may be used in an insulin pump replacement method as will become appreciated herein. Therefore, the disclosed embodiments of the insulin pump 1 and its operation also define corresponding embodiments of the insulin pumps 1 in an insulin infusion system and of the method for replacing a first insulin pump 1 by a second insulin pump 1. For example, the insulin pump 1 may be configured to perform the steps of searching for the presence of a source pump, and, when the presence of a source pump is detected, performing the steps of receiving, via the communication interface, an infusion program from the source pump, and storing the infusion program in the memory. An insulin pump of this type of embodiment may be capable of alternatively serving as both the first insulin pump 1 or the second insulin pump 1 in an insulin infusion system and a replacement method as described herein.

In one embodiment, the communication interface 60 via which an infusion program may be transmitted from a source pump to a replacement pump may comprise a wireless bidirectional communication interface 60 which can allow simple data exchange. The communication interface 60 may, for example, comprise a radio frequency interface according to a communication standards known in the art, such as the BLUETOOTH standard, or according to a proprietary standard. Alternatively, the wireless bidirectional communication interface 60 may comprise an infrared interface. In further alternative embodiments, the communication interface 60 may comprise a wired interface.

When a remote controller is present, data may be exchanged with the remote controller via the same communication interface 60 of the insulin pump 1. Alternatively, the insulin pump 1 may comprise a separate communication interface 60 for communicating with a remote controller. Thus, in one embodiment, the insulin pump 1 may be configured to receive its infusion program from a remote controller in the alternative to receiving it from a source pump 1.

As discussed above, an insulin pump 1 may act as source pump. In such embodiments, the control unit 40 may be configured to monitor, during operation of the insulin pump 1 according the infusion program, a status of the insulin pump 1 and to activate the search for the presence of a replacement pump 1 when a predetermined status is assumed by the insulin pump 1.

Furthermore, in one particular embodiment, searching for a replacement pump 1 may only occur if a predetermined status is assumed. Such an embodiment may limit energy consumption as well as avoid handling errors since it prevents an unintended program transfer. The status of the insulin pump 1 may also be checked in a test mode which is periodically activated by a timer of the control unit 40. Alternatively or additionally, the search for a replacement pump 1 may be activated by an interrupt signal which is generated when the predetermined status is assumed. In such an embodiment, a dedicated test mode may not be required.

In another embodiment, the status of the insulin pump 1 which may be monitored during operation may comprise a filling state of the insulin reservoir. In such an embodiment, a search for another pump to act as replacement pump may thereby be activated if the filing volume of the insulin reservoir falls below a predefined value of, e.g. 10%, of the maximum filling volume. In another embodiment, the status may further comprise an error status, such that the occurrence of an error condition, i.e. an occluded infusion cannula or a device error, may be periodically monitored and a search for another insulin pump may be activated upon the occurrence of an error condition.

In one exemplary embodiment, the status may further comprise the status of a battery 80 of the insulin pump 1. Such an embodiment may be utilized, for example, when the battery 80 is integral with the pump 1 and cannot be replaced. While the battery 80 capacity of these types of devices may include a safety factor to ensure that the battery 80 is not exhausted prior to the reservoir being empty, this situation may nonetheless occur if the battery is, due to improper assembly, partly discharged during assembly of the infusion pump, or due to a defective of the battery 80 itself, or the like. Therefore, the battery voltage may be monitored by a voltage monitoring unit in an analogue way to the filling volume of the insulin reservoir. Additionally or alternatively to the voltage, the energy effectively taken from the batter may be monitored by a gauging unit known in the art.

In some embodiments, the source pump 1 may transmit the status of the source pump to the replacement pump 1 along with the infusion program. For example, it may transmit an error code of an error which can result in the source pump activating the search for a replacement pump 1.

In another Embodiment, the insulin pump 1 may be designed such that insulin delivery may be continued during the search for a replacement pump 1. For example, if the search is activated because of the filling state of the insulin reservoir 30 falling below a predefined value as described above, the delivery may be continued until the program is transferred to a replacement pump 1 such that the insulin delivery is not interrupted longer than required.

The control unit 40 may also be alternatively or additionally configured to control the insulin pump 1 to terminate operation after successful transmission of the infusion program to the replacement pump 1. Terminating the operation may, for example, comprise stopping the insulin delivery, followed by switching off the pump or changing it a safe state. In one embodiment, it may further comprise an automated rejection of the infusion cannula by an inserter of the insulin pump.

As also discussed above, an insulin pump 1 may also act as a replacement pump 1. For example, in embodiments of the insulin pump 1 which allow the insulin pump 1 to act as replacement pump 1, the control unit 40 may be configured to control the insulin pump 1, after successfully having received an infusion program from the source pump 1, to automatically start insulin delivery. Starting the insulin delivery may additionally comprise preparative steps, in particular priming the infusion cannula with insulin and/or inserting the infusion cannula 11 into the patient's subcutaneous tissue by an automatic inserter of the insulin pump 1. Automatic insertion of the infusion cannula 11 may be employed, for example, if the insulin pump 1 is a patch pump which is secured to the patient's skin via an adhesive layer.

In another embodiment, an insulin pump 1 may allow for a simple replacement or exchange, and, thus, continuation of the therapy, without requiring the presence of a remote controller and without requiring the presence of operation elements, such as buttons or a display, on the pump. Thus, since all required steps are performed automatically under control of the two pumps, the patient may simply secure the newly programmed replacement pump 1 to his or her body after the transfer of the infusion program is complete.

In some embodiments where the infusion cannula 11 of the replacement pump 1 is automatically inserted into the skin, the control unit 40 of the replacement pump 1 may be configured to wait, after the replacement pump 1 has successfully received the infusion program, for a defined period of time before actuating the inserter. This defined period of time between the transfer of the program and the insertion of the cannula 11 may provide the patient sufficient time to secure the insulin pump to the body. For example, in one embodiment, a time period of 10-15 minutes may be provided. In another embodiment, a time period of longer than 15 minutes for insertion of the cannula may be provided. In yet another embodiment, shorter waiting time of less than 10 minutes may be provided.

As long as the insulin pump 1 which is acting as replacement pump 1 is not in use and has not received an infusion program from a remote controller or a source pump 1, it may be sustained in a low-energy mode. For example, as described above, disposable pumps may be provided with a readily built-in battery. Since the size of such a battery is limited by the overall device dimensions and the pump may be stored for several weeks or months prior to its use, providing the insulin pump low-energy mode may provide for minimum energy consumption and elongate the lifespan of the device.

In one embodiment, as the insulin pump 1 is in the low energy mode, the insulin pump 1 may be periodically switched into a search mode to detect the presence of a source pump 1 or remote controller. The time interval may, for example, be 1 second, 1 minute or 3 minutes. Similarly, an additional device for detecting another insulin pump may be activated periodically in a search mode. Setting the time interval may thereby require a compromise between a short delay for detecting the presence of a source pump on the one hand and low energy consumption on the other hand. Thus, the time delay may be adjusted based on the particular application of the insulin pump.

As discussed above, communication between a source pump 1 and a second pump 1 may allow for the transfer of the infusion program. In one embodiment both an insulin pump 1 acting as source pump 1 as well as an insulin pump 1 acting as replacement pump 1 may operate in a search mode. As used herein, the term 'search mode' is used for a mode where the pump searches for the presence of an other insulin pump 1, but a communication line has not yet been established. The search mode may be either active or passive. If the search mode is active, the insulin pump 1 may emit signals, such as infrared or radiofrequency signals, to be received and responded to by the other insulin pump 1. If the search mode is passive, the insulin pump 1 may wait for the reception of signals emitted by the other insulin pump 1 and responds to such received signals. In one embodiment, the search mode is active if the insulin pump 1 serves as a source pump 1. In another embodiment, the search mode is passive if the insulin pump 1 serves as a replacement pump 1. In yet another embodiment, other search mode assignments to the various insulin pumps may additionally or alternatively be made.

In some embodiments, the communication interface 60 which is used for transmitting the infusion program of the source pump 1 to the replacement pump 1 may also be used for detecting the presence of the other of the source pump 1 and the replacement pump 1, respectively. Alternatively, the insulin pump 1 may also have an additional device for detecting another insulin pump. In such an embodiment, the detection of another insulin pump 1 may take place independently of the communication interface 60 which is used for the data exchange. While requiring additional hardware, this may allow for the communication interface 60 only being activated after the detection of the other insulin pump 1 thereby providing additional energy consumption and safety.

In one embodiment, switches or sensors may be utilized to detect magnetic and/or electric fields. However, purely mechanical switches could additionally or attentively be provided, which may, for example, be activated by a coupling member, such as a notch, of the other insulin pump 1. In one particular embodiment, the device for detecting another insulin pump 1 may comprise a reed relay or a Hall sensor. For example, in one particular embodiment, a reed relay may be used to detect magnetic fields, that are generated, for example, by a permanent magnet or an electro magnet in the other insulin pump. This may provide a particularly energy-efficient embodiment as the reed relay itself does not require current, and the energy for changing the switch state may be introduced into the insulin pump from outside. In another particular embodiment, a Hall sensor may be used to detect the other insulin pump. In such an embodiment, when the Hall sensor has a current passed through it and is brought into a magnetic field running perpendicular to it, it may deliver an output voltage. A switch function may thus be obtained in combination with a transistor and/or further semi-conductor components known in the art. In this way, as in the case of the reed relay, the magnetic fields of permanent magnets arranged in the other insulin pump can be detected. The Hall sensor may allow for no mechanically movable parts that could be damaged such as, for example, if the insulin pump were accidentally dropped.

For embodiments comprising a magnetic-field sensitive switch or sensor, the device for detecting another insulin pump may further comprises a magnet, such as a permanent or an electro magnet for generating a magnetic field. The magnet may thereby activate the magnetic field-sensitive switch or sensor in the other insulin pump. By approaching the insulin pumps 1, the magnetic field generated by the magnet in either of the insulin pumps may activate the magnetic-field sensitive switch or sensor of the other the other insulin pump. In one embodiment, the magnet and the magnetic-field sensitive switch or sensor may be arranged in a substantially shielded position from each other or at sufficiently spaced positions from the insulin pump 1, such that the switch or sensor is not operated by the magnet of the same pump. The magnet and the magnetic-field sensitive switch or sensor may be designed for an activation distance of some centimeters or for activation only if the insulin pumps 1 touch each other. In one embodiment, a well defined orientation of the insulin pumps 1 with respect to each other may further be required for the magnetic-field sensitive switch or sensor to be activated.

In some embodiments, it may be sufficient if the magnetic-field sensitive switch or sensor of one of the pumps, for example the replacement pump, is activated by a magnetic field emitted by the other insulin pump 1. In some of those embodiments, the insulin pump may comprise, for example, an electro magnet which is powered only in the search mode. Alternatively, the insulin pump 1 may be designed such that a program transfer may only be performed if the magnetic-field sensitive switch or sensor of both of the two pumps is activated by the other of the two pumps.

In another embodiment, the device for detecting the other insulin pump 1 may be designed as an infrared interface. In addition, coded signals may also be transmitted with an infrared interface such that, before the actual data exchange via the bidirectional communication interface 60, it is possible to verify whether both communicating devices are compatible insulin pumps 1.

For embodiments comprising a switch which has to be activated before an infusion program can be transferred to it, a remote controller may be configured to activate the switch in the same or similar way as a source pump.

In embodiments comprising a switching element, such as a mechanical switch or a reed relay as device to detect the presence of another insulin pump 1, the insulin pump 1 may be switched off in the low-energy mode. Only activating the switch may result in the controller of the pump to be powered. Once the insulin pump is in operation, the components of the insulin pump 1 may be connected with the battery by a further relay, semiconductor switch, or the like, such that activation of the switch by en external energy is not further required. For this type of embodiment, the insulin pump may not consume any energy in the low-energy mode since it does not need to periodically activate a communication interface or a device for detecting another insulin pump since the energy for switching the switch and, thus, changing the operation mode of the insulin pump 1 is introduced into the insulin pump from outside, that is, from the other insulin pump 1.

In one particular embodiment in which the insulin pump comprises an electro magnet for activating a magnetic-field sensitive switch of another insulin pump 1, it may be designed such the electro magnet of the source pump is powered in the search mode, while the electro magnet of the replacement pump is not powered in the low-energy mode and search mode. Such an embodiment may not require the replacement pump to emit energy while in the low energy mode and thus require only minimum energy consumption of the unused replacement pump prior to its application. After the magnetic-field sensitive switch or sensor of the receiving pump has been activated by the source pump, it may optionally power its electro magnet to activate the magnetic-field sensor or switch of the source pump for acknowledging purposes.

As stated above, the insulin reservoir of the pump is typically in an initial empty state and is filled by the patient prior to use. In some embodiments, the insulin pump may be designed such that filling of the insulin reservoir is automatically detected. Upon detecting of the insulin reservoir being filled, the insulin pump may switch to the search mode. If the pump is of the syringe-driver type, a plug of the insulin reservoir may be in an initial most proximal position corresponding to an empty drug reservoir and displaced into a distal position if fluid is forced into the insulin reservoir, e.g., via a syringe. In such an embodiment, the pump may be designed such that this displacement of the plug operates an electrical contact which triggers the pump to switch to the search mode. Likewise, before the contact is operated, the insulin pump may be switched off.

In some embodiments, the insulin pump 1 may comprise indicators such as light emitting diodes, a buzzer or loud-speaker, a pager vibrator, or the like. Those indicators may be used to indicate one or multiple of a number of situations. In particular, the indicators may indicate at least one of the search for the replacement pump, the successful detection of the replacement pump, the successful transmission of the program to the replacement pump, or the unsuccessful transmission of the program to the replacement pump.

In embodiments of the insulin pump 1 which may act as replacement pump, an indication unit may be configured to indicate at least one of the search for the source pump being active, the establishment of communication with the source pump, the successful reception of the infusion program from the replacement pump, the unsuccessful reception of the infusion program from the replacement pump, or the start of insulin delivery.

While reference has been made herein to particular insulin delivery systems and insulin pumps, the utilization of such systems and pumps may provide for continuous therapy for a patient. For example, according in one embodiment, the method of replacing a first insulin pump with a second insulin pump may comprise the steps of operating the first insulin pump according to an infusion program stored in a memory 42 of the first insulin pump, and autonomously performing the steps of activating a search for the presence of the second insulin pump, and, upon detection of the presence of the second insulin pump transmitting, via communication interfaces 60 of the first insulin pump and the second insulin pump, the infusion program from the first insulin pump to the second insulin pump.

In another embodiment, the method may further comprise the step of monitoring, during operation of the first insulin pump according the infusion program, a status of the first insulin pump and activating the search for the presence of the second insulin pump when a predetermined status is assumed by the first insulin pump. For such an embodiment, the search for the presence of the second insulin pump is carried out if the status of the first insulin pump indicates that it should be replaced by the second insulin pump.

Referring now to FIG. 1 (i.e., FIGS. 1a, 1b, 1c and 1d), a schematic illustration of transitioning between a first insulin pump 505 and a second insulin pump 505' is shown. Specifically, FIG. 1a depicts a first insulin pump 505 in accordance with one exemplary embodiment which may be attached to the skin 502 of a patient and is presently in the delivery mode. The first insulin pump 505 may have received its infusion program from a remote controller 510 or from a previously used insulin pump. The additional infusion of insulin boli, as well as further programming and control capabilities for the first insulin pump 505, may be available via the remote controller 510. FIG. 1b further depicts a second insulin pump 505' which is of the same type as the first insulin pump 505. The second insulin pump 505' may be provided, for example, in a sterile box 515 and in a low-energy mode or sleeping mode.

FIG. 1b depicts a later situation where a status of the first insulin pump 505 is such that it may be replaced due to the filling state of its insulin reservoir, the status of the battery and/or the occurrence of an error condition. In such a condition, the first insulin pump 505 may give an indication to the patient via an acoustical and/or optical indicator and activate the search for a second insulin pump. Upon the indication, the patient may remove the second insulin pump 505' from its sterile box 515 and transition it towards the first insulin pump 505. Prior to performing this step, the patient may also fill the insulin reservoir of the replacement pump 505' if it was initially empty. In the following, the first insulin pump 505 acts as source pump while the second insulin pump 505' acts as replacement pump. The presence of the replacement pump 505' may be detected by the source pump 500 and communication may be established as indicated by the arrows 520.

After establishing the communication, the source pump 505 may transfer the infusion program to the replacement pump 505' as indicated in FIG. 1c by arrow 525. After successful transmission of the infusion program, the source pump 505 may terminate its operation.

The final steps of the exemplary replacement procedure are shown in FIG. 1d. Specifically, the patient may remove the source pump 505 from its skin 502 and discard it, as indicated by arrow 530. The patient may then attach the replacement pump 505' to his or her skin 502. After a delay of some minutes, the replacement pump 505' may carry out preparative steps, such as, for example, priming its infusion cannula with insulin and inserting the infusion cannula into the patient's subcutaneous tissue and subsequently start insulin infusion. If the insulin pumps do not comprise an infusion cannula which is automated inserted into the patient's tissue, this step may be carried out manually by the patient.

Figure 5:
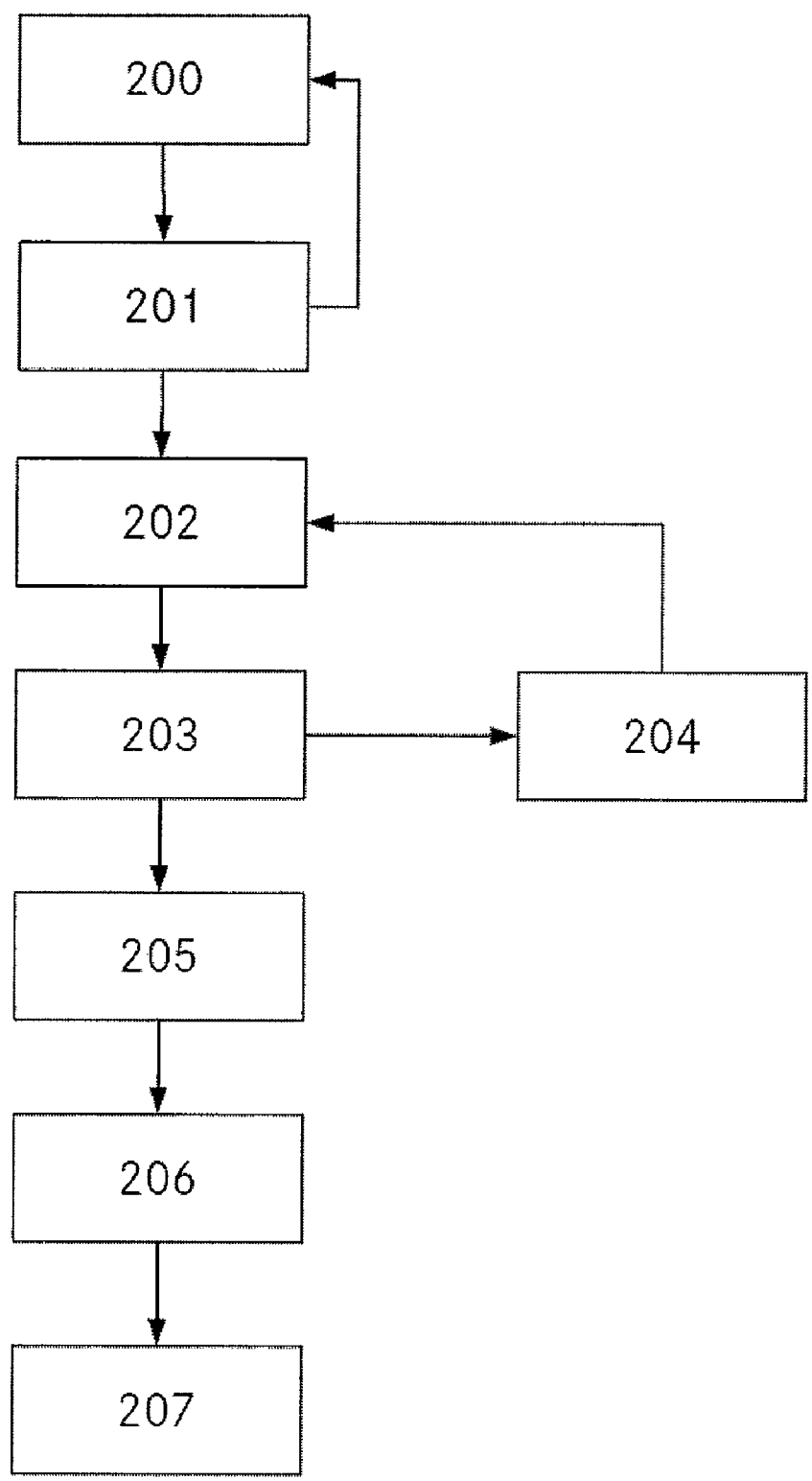
FIG. 5 depicts a schematic sequence of deactivation of a source pump which is in delivery mode, with the insulin reservoir almost used up, and which is exchanged for a new replacement pump according to one or more embodiments shown and described herein.

Referring now to FIGS. 2-5, an exemplary method is illustrated in FIG. 5 in which the insulin pump 1 functions as the source pump. Specifically, the insulin pump 1 may initially be in the delivery mode 200. The insulin pump 1 may then deliver insulin 32 via the delivery device 20 and supply the patient with the required doses of insulin 32 in accordance with a basal delivery schedule which is stored as infusion program in the memory unit 42. On the basis of the number of control impulses already sent to the delivery device 20, the control unit 40 additionally determines the filling state of the insulin 32 in the insulin reservoir 30. In one embodiment, the light-emitting diode 70 (when present) may be additionally used to signal the delivery mode.

In the subsequent test mode 201, the determined filling state of the insulin reservoir may be compared to a minimum value stored in the memory unit 42. If the filling state is greater than or equal to the minimum value, the operation may be changed back to the delivery mode 200 and the filling state may be determined again after a period of time and/or after a following insulin delivery. However, if the control unit 40 determines in the test mode 201 that the filling state is less than the minimum value stored in the memory unit 42, the first interface activation 202 may take place in which the infrared interface 50 is switched on. In the same way, the occurrence of an error condition, such as a device error or an occluded cannula, may be monitored in the test mode 201. Optionally, the state of the battery 80 may also be determined and compared to a minimum value in an analogue way to the insulin reservoir.

The control unit 40 may then change to the search mode 203, in which the insulin pump 1 searches for an infrared signal from a second and unused replacement pump. If no such signal is detected, the control unit 40 may change to the interface deactivation mode 204. In the interface deactivation mode 204, the infrared interface 50 may be first switched off and then after a period of 2 minutes, for example, may be allowed to elapse before the control unit 40 performs the first interface activation 202 again.

As soon as an infrared signal of a replacement pump is detected during the search mode 203, the insulin pump 1 may test whether the infrared signal has a known and valid code. If no code is recognized, the insulin pump 1 may change back to the interface deactivation mode 204. However, if the code of the infrared signal is recognized by the insulin pump 1, the control unit 40 may change to the connection mode 205. An acknowledgement signal may be sent to the replacement pump via the infrared interface 50, and the radiofrequency interface 60 may then switched on. A connection to the replacement pump detected by the infrared interface 50 may then be set up via the radiofrequency interface 60. Among other things, the data transfer rates may be established on the basis of the signal quality.

In the subsequent transmit mode 206, the infusion program stored in the memory 42 of the insulin pump 1 may be transferred to the replacement pump via the radiofrequency interface 60. After the data transfer has taken place, the insulin pump 1 may change to the switch-off mode 207 in which operation of the insulin pump 1 is terminated. In the switch-off mode 207, a standby time, for example of 2 minutes, may be allowed to elapse. The control unit 40 may then deactivate the delivery device 20 and thus stop the delivery of insulin 32. Thereafter, the control unit 40 may optionally cause the inserter 10 to retract the cannula 11. The control unit 40 may then emit an acoustic signal via the sound generator 71 to indicate termination of the operation and switch off all the other components of the insulin pump 1. The insulin pump 1 can then be removed by the patient from his or her body and, for example, replaced by the replacement pump.

The insulin pump 1 may thus supply the patient with insulin throughout all the method steps or modes 200-206 illustrated in FIG. 2, except in the switch-off mode 207. In case of an error, the insulin delivery may be terminated and the insulin pump may emit an alert signal via the sound generator 71 and/or the light-emitting diode 70 throughout the modes 200-206. Alternatively, insulin supply may be stopped between establishing the connection in step 205 and transmitting the program in step 206.

Figure 6:
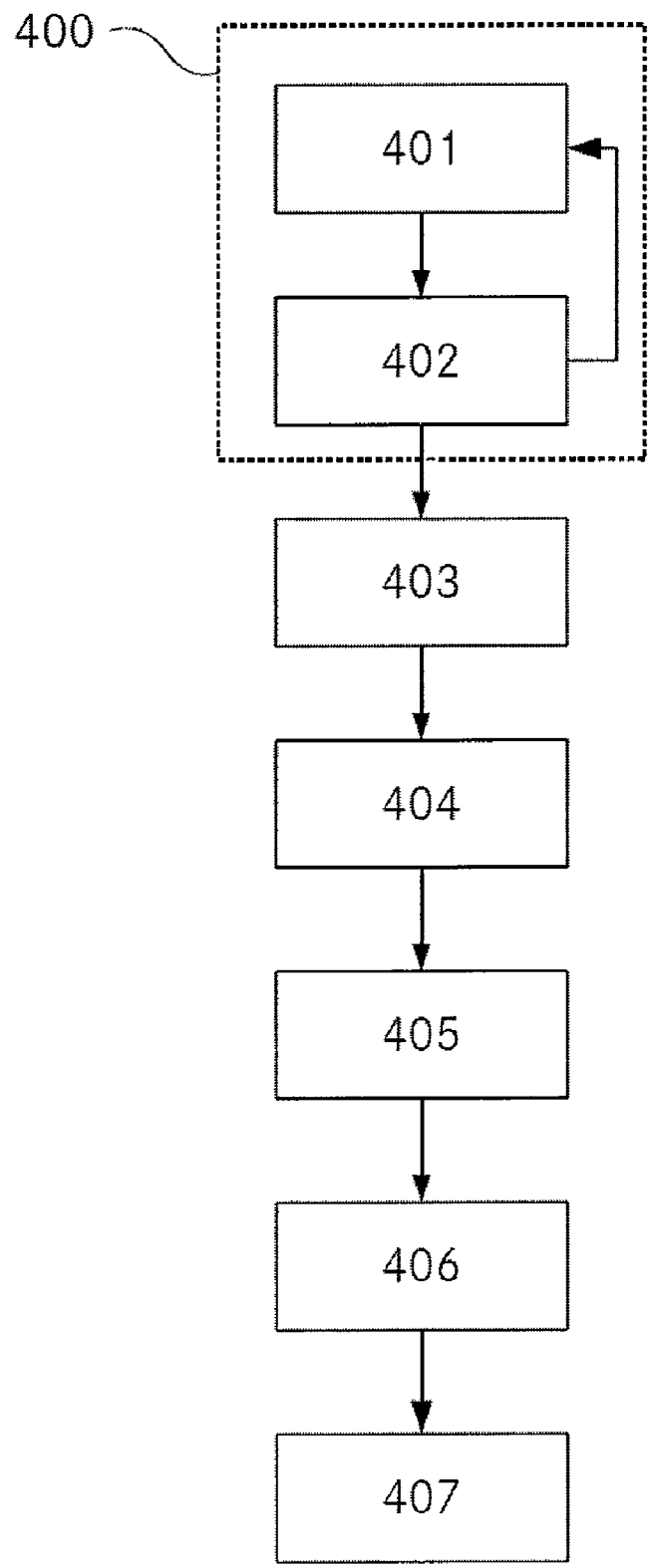
FIG. 6 depicts a schematic sequence of the steps involved in the activation of the new replacement pump according to one or more embodiments shown and described herein.

Referring now to FIGS. 2-4 and 6, an exemplary method is illustrated in FIG. 6 in which the insulin pump 1 functions as the replacement pump. Specifically, the method illustrated in FIG. 6 shows the mode of operation of the insulin pump 1 (as a replacement pump) provided in the unused state and upon first activation. After production, the insulin pump 1 may be in the low-energy mode 400 and not yet possess a patient-specific program in its storage. In a first step 401, a coded infrared signal may be emitted via the infrared interface 50 in the low-energy mode 400. In the second step 402 of the low-energy mode 400, the infrared interface 50 may search for an acknowledgement signal from another insulin pump (which acts as source pump and accordingly has a patient-specific program). If no acknowledgement signal is detected, the first step 401 of the low-energy mode 400 may be performed again. The steps 401 and 402, form in combination, a search mode of the insulin pump 1. The steps may optionally be performed only after filling of the insulin reservoir 30 of the insulin pump 1 by the patient has been detected. In such an embodiment, the low-energy mode may thereby be equivalent with the search mode. In an other embodiment, the acknowledgement signal received in the second step 402 of the low-energy mode 400 may originate from a remote controller and, accordingly, the program may transfer from the operating appliance to the insulin pump in the receive mode. This may comprise the normal case where an operational remote controller is present.

As soon as an acknowledgement signal is detected in the second step 402 of the low-energy mode 400, the control unit 40 may activate the radiofrequency interface 60 in the switch-on step 403. A connection may then be set up with the other insulin pump detected by the infrared interface 50 and, among other things, the data transfer rate may be established on the basis of the signal quality.

In the subsequent receive mode 404, the program of the other insulin pump may be transferred to the insulin pump 1 via the radiofrequency interface 60 and stored in the memory unit 42. The program may include in particular the time and date as well as the basal delivery schedule.

Thereafter, the control unit 40 may change to standby mode 405, during which the insulin pump 1 shows no activity for a period of, for example, 15 minutes. The standby mode 405 may give a patient sufficient time to apply the insulin pump 1 to the desired location on the body. After the 15 minutes have passed, the insulin pump may change automatically to the use mode 406, in which the control unit 40 causes the inserter 10 to deploy the cannula 11 and thus insert it into the patient's body. Before changing to the standby mode 405, the cannula 11 may optionally be automatically primed in order to displace the air in the cannula 11 by insulin.

The control unit 40 may then change to start-up mode 407. The delivery device 20 may thereby be activated by the control unit 40 and deliver insulin 32 from the insulin reservoir 30 into the cannula 11 according to the program stored in the memory unit 42. The control unit 40 may also emit an acoustic signal via the sound generator 71 and optionally indicate beginning of the delivery via the light-emitting diode 70. The control unit may then change to the delivery mode 200 described in FIG. 5.

With respect to FIG. 5, the insulin pump, may, in the search mode 203, emit an infrared signal to be detected by a replacement pump rather than searching for an infrared signal emitted by a replacement pump, followed by searching for the reception of an acknowledgement signal to be sent by a replacement pump.

In an analogue way, with respect to FIG. 6, the insulin pump 1 may, in the mode 401, detect if an infrared signal is received from a source pump rather than emitting a signal. In such an embodiment, the step 402 may be omitted. An acknowledgement signal is, in this case, emitted by the insulin pump 1 in the switch-on-step 403.

As discussed above, other devices for providing signals and information to the user can be used instead of or in addition to the light-emitting diode 70 or the sound generator 71. For example, in one embodiment, the sound generator 71 can be replaced by a tactile element, such as a mechanical vibrator. In another embodiment, a screen may be provided for displaying symbols or texts which, for example, provide information on the operating state of the insulin pump. Furthermore, in another embodiment, the infrared interface 50 for detection of a replacement pump may be omitted and a reed relay or a Hall sensor may be provided as discussed above. In such an embodiment, a permanent magnet may also be disposed in the interior of the housing 2, such that the insulin pump 1 can also be detected by a replacement pump. The reed relay or Hall sensor may thus be activated only when a filling state of an insulin reservoir of the source pump falls below a predefined minimum value, in particular 10%, and/or on the occurrence of an error condition or another predetermined status of the source pump. Such an embodiment may allow for the reduction in the risk of inadvertent actuation through magnetic interference sources.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An insulin delivery system comprising a first insulin pump and a second insulin pump, wherein each of the first insulin pump and the second insulin pump comprises:
   a memory configured to store an infusion program;
   a control unit configured to control operation of the insulin pump; and
   a communication interface for data exchange with the other of the first insulin pump and the second insulin pump;
   wherein the control unit of the first insulin pump is configured to autonomously:
      monitor, during operation of the first insulin pump according to the infusion program, a status of the first insulin pump;
      activate a search for the presence of the second insulin pump when a predetermined status is assumed by the first insulin pump, wherein the control unit is further configured to control the first insulin pump to continue insulin delivery according to the infusion program during the search for the presence of the second insulin pump is active; and, upon detection of the presence of the second insulin pump, transmit, via the communication interface of the first insulin pump, the infusion program stored in the memory of the first insulin pump to the second insulin pump; and the control unit of the second insulin pump is configured to:
search for the presence of the first insulin pump, and,
upon detection of the presence of the first insulin pump,
receive, via the communication interface of the second insulin pump, an infusion program from the first insulin pump; and
store the infusion program in the memory of the second insulin pump.

2. The insulin delivery system of claim 1, wherein the first insulin pump and the second insulin pump are identical insulin pumps.

3. A method for replacing a first insulin pump by a second insulin pump, the method comprising:
operating the first insulin pump according to an infusion program stored in a memory of the first insulin pump; and
controlling the first insulin pump to autonomously perform the steps of:
activating a search for the presence of the second insulin pump, wherein the first insulin pump continues to operate to delivery insulin according to the infusion program during the search for the presence of the second insulin pump is active, and, upon detection of the presence of the second insulin pump; and
transmitting, via communication interfaces of the first insulin pump and the second insulin pump, the infusion program from the first insulin pump to the second insulin pump.

4. An insulin pump comprising:
a communication interface for data exchange with a replacement pump;
a memory configured to store an infusion program; and
a control unit configured to control operation of the insulin pump, wherein the control unit is further configured to autonomously:
monitor, during operation of the infusion pump according to the infusion program, a status of the insulin pump;
activate a search for the presence of the replacement pump when a predetermined status is assumed by the insulin pump, wherein the control unit is further configured to control the insulin pump to continue insulin delivery according to the infusion program during the search for the presence of the replacement pump is active; and
transmit, upon detecting the presence of the replacement pump, via the communication interface, the infusion program stored in the memory to the replacement pump.

5. The insulin pump of claim 4, wherein the status monitored by the control unit comprises at least one of a filling state of an insulin reservoir of the insulin pump, the status of a battery of the insulin pump, and an error status of the insulin pump.

6. The insulin pump of claim 5, wherein the control unit is further configured to control the insulin pump to continue insulin delivery while a search for the presence of the replacement pump is active.

7. The insulin pump of claim 6, wherein the control unit is further configured to control the insulin pump to terminate operation after successful transmission of the infusion program to the replacement pump.

8. The insulin pump of claim 7, wherein the insulin pump comprises, in addition to the wireless communication interface, a device for detecting the presence of the replacement pump.

9. The insulin pump of claim 8, wherein the insulin pump is further configured to receive the infusion program from a remote controller.

10. The insulin pump of claim 9, wherein the control unit is further configured to indicate, via an indicator of the insulin pump, at least one of the search for the replacement pump, the successful detection of the replacement pump, the successful transmission of the program to the replacement pump, or the unsuccessful transmission of the program to the replacement pump.

11. The insulin pump of claim 4, wherein the control unit is further configured to control the insulin pump to terminate operation after successful transmission of the infusion program to the replacement pump.

12. The insulin pump of claim 4, wherein the insulin pump comprises, in addition to the wireless communication interface, a device for detecting the presence of the replacement pump.

13. The insulin pump of claim 4, wherein the insulin pump is further configured to receive the infusion program from a remote controller.

14. The insulin pump of claim 4, wherein the control unit is further configured to indicate, via an indicator of the insulin pump, at least one of the search for the replacement pump, the successful detection of the replacement pump, the successful transmission of the program to the replacement pump, or the unsuccessful transmission of the program to the replacement pump.

15. The insulin pump of claim 4, wherein the insulin pump is further configured to:
search for the presence of a source pump; and
when the presence of a source pump is detected, receive, via the communication interface, an infusion program from the source pump; and
store the infusion program in the memory.

16. The insulin pump of claim 15, wherein the control unit is further configured to detect an insulin reservoir of the insulin pump being filled, and, upon the insulin reservoir being filled, to activate the search for a source pump.

17. The insulin pump of claim 15, wherein the control unit is further configured to control the insulin pump, after successfully having received an infusion program from the source pump, to autonomously start insulin delivery.

18. The insulin pump of claim 17, wherein the control unit is further configured to detect an insulin reservoir of the insulin pump being filled, and, upon the insulin reservoir being filled, to activate the search for a source pump.

* * * * *

UNITED STATES PATENT AND TRADEMARK OFFICE
CERTIFICATE OF CORRECTION

| | | |
|---|---|---|
| PATENT NO. | : 8,118,782 B2 | |
| APPLICATION NO. | : 12/875713 | |
| DATED | : February 21, 2012 | |
| INVENTOR(S) | : Axel Remde | |

It is certified that error appears in the above-identified patent and that said Letters Patent is hereby corrected as shown below:

Col. 2, Line 39, "embodiment An insulin" should read --embodiment, an insulin--

Col. 4, Line 44, "may also arranged" should read --may also be arranged--

Col. 5, Line 22, "according the" should read --according to the--

Col. 6, Line 46, "a communication standards" should read --a communication standard--

Col. 6, Line 61, "may act as source pump" should read --may act as a source pump--

Col. 6, Line 64, "according the" should read --according to the--

Col. 7, Line 15, "as replacement pump" should read --as a replacement pump--

Col. 7, Line 16, "filing volume" should read --filling volume--

Col. 7, Line 33, "defective" should read --defect--

Col. 7, Line 36, "batter" should read --battery--

Col. 7, Line 43, "Embodiment" should read --embodiment--

Col. 7, Line 55, "Changing it a safe state" should read --Changing it to a safe state--

Col. 8, Line 55, "an other" should read --another--

Col. 9, Line 15, "or attentively" should read --or alternatively--

Col. 9, Line 40, "may further comprises" should read --may further comprise--

Col. 9, Line 46, delete "the other"

Line 10, Line 30, "such the" should read --such that the--

Signed and Sealed this
Fourteenth Day of August, 2012

David J. Kappos
*Director of the United States Patent and Trademark Office*

CERTIFICATE OF CORRECTION (continued)
U.S. Pat. No. 8,118,782 B2

Col. 10, Line 63, "act as replacement pump" should read --act as a replacement pump--

Col. 11, Line 7, "according in one" should read --according to one--

Col. 11, Line 19, "according the infusion" should read --according to the infusion--

Col. 12, Line 4, "automated inserted" should read --automatically inserted--

Col. 12, Line 51, "may then switched on" should read --may then be switched on--

Col. 13, Line 33, "In an other" should read --In another--

Col. 15, Claim 3, Line 29, "to delivery" should read --to deliver--